United States Patent [19]

Weisang et al.

[11] 3,957,900
[45] May 18, 1976

[54] METHOD FOR THE DEHYDRATION OF DIOLS

[75] Inventors: Joseph Edouard Weisang; Georges Szabo, both of Le Havre; Jean Maurin, Montivilliers, all of France

[73] Assignee: Compagnie Francaise de Raffinage, France

[22] Filed: Jan. 21, 1975

[21] Appl. No.: 542,717

Related U.S. Application Data

[60] Division of Ser. No. 396,219, Sept. 11, 1973, Pat. No. 3,893,946, which is a continuation of Ser. No. 132,892, April 9, 1971, Pat. No. 3,781,222.

[30] Foreign Application Priority Data

Apr. 16, 1970  France .............................. 70.13791

[52] U.S. Cl................................ 260/681; 252/437; 260/642 R
[51] Int. Cl.² ...................... C07C 1/24; C07C 29/00
[58] Field of Search ............................ 260/681, 642

[56] References Cited

UNITED STATES PATENTS

| | | | |
|---|---|---|---|
| 3,758,612 | 9/1973 | Maurin ............................... | 260/681 |
| 3,781,222 | 12/1973 | Weisang et al. ................... | 260/681 |
| 3,846,338 | 11/1974 | Kachlova et al. .................. | 260/681 |

*Primary Examiner*—D. Horwitz
*Attorney, Agent, or Firm*—Curtis, Morris & Safford

[57] ABSTRACT

Method for dehydrating diols into diolefins and/or olefin alcohols by contacting said diols under dehydration conditions with a catalyst prepared by forming an intimate mixture of finely divided solid particles of at least one pyrophosphate and at least one acid orthophosphate of at least one metal belonging to the group consisting of lithium, sodium, strontium, and barium into a formed mass which is thereafter calcined to transform the acid orthophosphate into pyrophosphate.

9 Claims, No Drawings

METHOD FOR THE DEHYDRATION OF DIOLS

This is a division of application Ser. No. 396,219, filed Sept. 11, 1973, now issued as Pat. No. 3,893,946, on July 8, 1975, which in turn is a continuation of the prior copending application Ser. No. 132,892, filed Apr. 9, 1971, now issued as Pat. No. 3,781,222, on Dec. 25, 1973.

The present invention relates to catalysts for the dehydration of organic compounds. More particularly, it concerns catalysts for the dehydration of diols, which diols may or may not be vicinal diols.

In the following description there will be described more particularly the application of the catalysts of the present invention to the dehydration of 2-methyl-2,3-butanediol due to the importance which it has. It is known that dehydration of 2-methyl-2,3-butanediol gives isoprene. Isoprene is a monomer which is greatly in demand both for the manufacture of synthetic "natural" rubber and for the manufacture of very diverse, high polymers. This particular application is, however, not a limitation on the invention, and the invention can actually be applied to other compounds, for instance, to the dehydration of 2,3-butanediol to give butadiene.

Ordinary dehydration catalysts, such as thoria or alumina, cannot be used for the dehydration of 2-methyl-2,3-butanediol or vicinal diols in general. They lead to excessive quantities of by-products, such as methyl isopropyl ketone and trimethyl acetaldehyde. Moreover, the application of lithium phosphate $Li_3PO_4$, known to be an isomerization dehydration catalyst of 2-methyl-2,3-epoxy butane into isoprene, for the dehydration of 2-methyl-2,3-butanediol produces isoprene only in a low yield if the lithium phosphate is prepared without special precautions. One of the applicants, in his application Ser. No. 30,276, filed Apr. 20, 1970 now abandoned, (and based on French patent application filed on Apr. 22, 1969, under National Registration No. 69,12684) has described a method of preparing trilithium orthophosphate which provides a compound which is much more active in the dehydration.

An object of the present invention is to improve the selectivity of the dehydration of diols. Another object is to stabilize the behavior of the catalysts with time.

The applicants have found that certain pyrophosphates have very good dehydrating properties.

One aspect of the present invention is, therefore, a dehydration catalyst comprising as dehydrating substance at least one neutral pyrophosphate, mixed or not, of at least one metal belonging to the group consisting of lithium, sodium, strontium, and barium.

The pyrophosphate is referred to as mixed when its molecule comprises several cations and when it constitutes a well-defined phase having characteristics of its own. It is called non-mixed when it is formed of molecules comprising only a single type of cation or of a purely physical mixture of molecules, each having only a single type of cation, which may be different from one molecule to the other.

Another aspect of the invention consists of the application of the catalyst described above to the dehydration of vicinal or non-vicinal diols and, more particularly, 2-methyl-2,3-butanediol.

Certain pyrophosphates are friable and, therefore, lend themselves poorly to lengthy use in a dehydration reactor. The applicant alleviates this drawback by a special preparation of the catalyst.

Another aspect of the present invention is, therefore, a method of preparing the catalyst just described above. This catalyst is obtained from at least one pyrophosphate and at least one acid orthophosphate, wherein at least one metal belongs to the group consisting of lithium, sodium, strontium, and barium. In this method the pyrophosphate and the acid orthophosphate are mixed in powder form; the resultant mixture is extruded, dried, and then calcined so as to transform the acid orthophosphate into pyrophosphate.

The following pyrophosphates, cited by way of illustration and not of limitation, fall within the scope of the invention: lithium neutral pyrophosphate, sodium neutral pyrophosphate, and barium neutral pyrophosphate, as well as the mixed pyrophosphate of lithium and sodium. The alkaline or alkaline earth pyrophosphate may be the only component of the catalyst, but this is not necessary; it is sufficient for it to form just a part of the composition of the catalyst. The mixing of a pyrophosphate described above and of a neutral orthophosphate of one of the aforesaid metals therefore falls within the scope of the invention. In particular, the addition of one of the above-mentioned pyrophosphates to trilithium orthophosphate makes it possible to avoid the decrease with time of the selectivity of the dehydration reaction of the trilithium orthophosphate.

The catalysts in accordance with the invention may be obtained by a wet method from sodium pyrophosphate. Thus, for instance, the catalyst consisting of a mixed pyrophosphate of lithium and sodium is obtained by reacting lithium hydroxide or a lithium salt, such as the chloride, acetate, or nitrate in solution, at a temperature of about 90°C. with the sodium pyrophosphate in aqueous solution and then drying and calcining the resultant precipitate. In the same manner, the addition with heat of a soluble barium salt to the sodium pyrophosphate in solution gives barium pyrophosphate.

Other methods of preparation can be used. Thus the drying and calcining of a mixture of lithium hydroxide and monoammonium orthophosphate gives lithium pyrophosphate. Barium pyrophosphate can be prepared by thermal dehydration of barium acid orthophosphate. Likewise, sodium pyrophosphate can be obtained by the calcining of sodium acid orthophosphate.

The coprecipitation of pyrophosphate and orthophosphate in variable proportions also produces a catalyst in accordance with the invention. One can thus, for instance, coprecipitate the mixed pyrophosphate of lithium and sodium and the trilithium orthophosphate by adding hot lithium hydroxide to a hot solution or orthophosphoric acid and sodium pyrophosphate, then drying and then calcining the resultant precipitate.

The physical properties of the catalysts of the invention depend on the nature of the cations which enter into the composition of the pyrophosphates. It is advantageous to obtain a catalyst which is insoluble in water and the melting point of which is far above the temperature at which the catalyst is used.

In order to improve the mechanical properties of the pyrophosphates, the coprecipitating of the pyrophosphate with a neutral orthophosphate, for instance a trilithium orthophosphate, is advantageous.

One method of preparing a catalyst which has good mechanical properties consists in intimately mixing a pyrophosphate powder of the type mentioned above and an acid orthophosphate powder of the same metals in any desired proportions and then wetting the mixture to obtain a paste which is then extruded. The catalyst is next dried and then calcined. The acid orthophosphate is transformed into pyrophosphate, which is the active component in the dehydration process.

For effective dehydration of vicinal diols into diolefins, it has be ascertained that neutrality is a necessity, i.e. neutral pyrophosphates must be used.

The catalytic dehydration of the diols is effected in vapor phase, the diol being either in pure state or diluted in an inert gas (for instance, nitrogen). The dehydration temperature is between 350° and 800°C and preferably between 400° and 500°C. The hourly space velocity, which measures the volume of liquid diol passing over a unit volume of the catalyst in one hour, is between 0.5 and 2.5

The following examples, which are not given by way of limitation, illustrate the preparation of the catalysts and the dehydration of 2 methyl-2,3-butanediol by means of the catalysts in accordance with the invention.

EXAMPLE I

This example concerns the preparation of double pyrophosphate of lithium and sodium of the formula $Li_3NaP_2O_7$ and the application thereof for the dehydration of 2-methyl-2,3-butanediol.

A quantity of 44.6 g of sodium pyrophosphate decahydrate is dissolved in 100 cc of distilled water at the boiling point. This hot solution is then added with agitation to 400 cc of a hot solution of a lithium salt containing 2.1 g of lithium. After cooling, the precipitate is filtered. In the event that the lithium salt is the chloride, the precipitate is washed with 200 cc of alcohol at 96° so as to eliminate the traces of sodium chloride. The precipitate is dried for 18 hours at 110°C and then calcined for 2 hours at 500°C.

Four catalysts were prepared by this method using lithium chloride, nitrate, acetate, and hydroxide, respectively.

These four catalysts were subjected one after the other to the following test: 10 cc, measured in liquid state, of 2-methyl-2,3-butanediol, entrained by a stream of nitrogen at a rate of flow of 4.8 liters per hour, were caused to flow for 1 hour at constant rate of flow over 10 cc of catalyst. This dilution corresponds to a partial pressure of one-third atmosphere for the diol and two-thirds atmosphere for the nitrogen. The dehydration is carried out at 400°C. The products obtained are analyzed by vapor-phase chromatography.

The results obtained with the different catalysts have been set forth in Table I below. These results concern the composition of the efflux collected between the thirtieth and sixtieth minutes in the different experiments. Successively entered therein are the conversion of the 2-methyl-2,3-butanediol, the yields of isoprene, 2-methyl-1-butene-3-ol, 3-methyl-2-butene-1-ol, trimethyl acetaldehyde and methyl isopropyl ketone. The conversion is expressed in number of mols per 100 mols of diol used. The yields are expressed in number of mols per 100 of diol converted.

TABLE I

| Lithium salt used in the synthesis of $Li_3NaP_2O_7$ | LiCl | $LiNO_3$ | $LiCH_3COO$ | LiOH |
|---|---|---|---|---|
| Conversion of diol | 100% | 100% | 100% | 100% |
| Yield of isoprene | 85.5 | 40.4 | 82.8 | 88 |

TABLE I-continued

| Lithium salt used in the synthesis of $Li_3NaP_2O_7$ | LiCl | $LiNO_3$ | $LiCH_3COO$ | LiOH |
|---|---|---|---|---|
| Conversion of diol | 100% | 100% | 100% | 100% |
| Yield of 2-methyl-1-butylene-3-ol | — | 39.9 | 1.0 | — |
| Yield of 3-methyl-2-butylene-1-ol | — | 5.2 | — | — |
| Yield of trimethyl acetaldehyde | 1.7 | 1.4 | 2.5 | 1.8 |
| Yield of methyl isopropyl ketone | 11.6 | 9.9 | 13.4 | 10.2 |

The two olefin alcohols can be recycled and dehydrated to form isoprene over the same catalyst with a yield which is close to 100 percent. Therefore, the nature of the lithium salt from which one starts to prepare the pyrophosphate is not of great importance.

EXAMPLE II

To 100 cc of a boiling solution of 44.6 g of dehydrated sodium pyrophosphate is added 400 cc of an equally hot solution containing 52.2 g of barium nitrate. The solution is set aside for a few hours, whereupon the precipitate is filtered and dried at 110°C for 18 hours. Calcining is effected at 500°C for 2 hours.

The use of this catalyst in the dehydration of 2-methyl-2,3-butanediol under conditions similar to those described in Example I gives an efflux whose average composition between the thirtieth and sixtieth minutes of the experiment is set forth in Table II below.

TABLE II

| Conversion of diol | 100% |
|---|---|
| Yield of isoprene | 7.6 |
| Yield of 2-methyl-1-butylene-3-ol | 76.0 |
| Yield of 3-methyl-2-butylene-1-ol | 4.2 |
| Yield of trimethyl acetaldehyde | 2.0 |
| Yield of methyl isopropyl ketone | 8.2 |

The conversion of the diol is complete, as in Example I.

EXAMPLE III

This example concerns a catalyst consisting of lithium pyrophosphate: $Li_4P_2O_7$.

A mixture of monoammonium orthophosphate and lithium hydroxide is subjected to calcining at a temperature above 400°C.

The lithium pyrophosphate obtained is subjected to the catalyst test described in Example I. The results obtained have been entered in Table III.

TABLE III

| Conversion of diol | 100% |
|---|---|
| Yield of isoprene | 67.4 |
| Yield of 2-methyl-1-butylene-3-ol | 5.6 |
| Yield of 3-methyl-2-butylene-1-ol | — |
| Yield of trimethyl acetaldehyde | 4.8 |
| Yield of methyl isopropyl ketone | 22.6 |

EXAMPLE IV

The average compositions of certain fractions of the efflux are indicated in Table V, below:

TABLE V

| Fraction analyzed | 0 to 30 min. | 3½ to 4 hours | 5½ to 7 hours | 7 to 7½ hours | 10½ to 11 hours | 13½ to 14 hours |
| --- | --- | --- | --- | --- | --- | --- |
| Conversion of diol | 91% | 26.4% | 86.5% | 90.3% | 86.6% | 84.8% |
| Yield of isoprene | 30.0 | 17.7 | 16.1 | 19.0 | 17.5 | 16.0 |
| Yield of 2-methyl-1-butylene 3-ol | 38.0 | 49.3 | 50.2 | 47.6 | 49.4 | 50.6 |
| Yield of 3-methyl-2-butylene-1-ol | 6.1 | 6.3 | 5.8 | 6.7 | 6.2 | 6.2 |
| Yield of trimethyl acetaldehyde | 4.8 | 4.8 | 5.2 | 4.8 | 4.8 | 5.0 |
| Yield of methyl isopropyl ketone | 17.8 | 18.2 | 18.3 | 18.4 | 18.5 | 18.8 |

This example concerns the preparation of a catalyst containing pyrophosphate and orthophosphate, as well as the use of the resulting catalyst for the dehydration of a diol. 500 milliliters of very hot solution containing 42 g of lithium hydroxide monohydrate are added to 350 cc of a very hot solution containing 57.7 g of 85 percent orthophosphoric acid and 111.5 g of sodium pyrophosphate decahydrate. After cooling, the resultant precipitate is filtered and then dried at 110°C for 18 hours and finally calcined at 600°C for 2 hours.

The coprecipitate of mixed sodium and lithium pyrophosphate and of trilithium orthophosphate is used as dehydration catalyst for 2-methyl-2,3-butanediol in accordance with the method described in Example I. The results obtained are set forth in Table IV below.

TABLE IV

| Conversion of diol | 100% |
| --- | --- |
| Yield of isoprene | 82.0 |
| Yield of trimethyl acetaldehyde | 1.9 |
| Yield of methyl isopropyl ketone | 15.1 |

EXAMPLE V

The catalyst consisting of mixed lithium and sodium pyrophosphate is friable. It is, therefore, necessary to improve its mechanical strength. This improvement is effected in the following manner: mixed lithium and sodium pyrophosphate is mixed with an equal weight of hydrated disodium orthophosphate of the formula $Na_2HPO_4$ and $7H_2O$. The mixture is crushed and then wetted with distilled water. The resultant paste is then extruded and then dried for 18 hours at 110°C and, finally, calcined at 500°C for 2 hours.

The catalyst thus obtained is of very good mechanical strength. It consists primarily of a mixture of lithium and sodium pyrophosphate and sodium pyrophosphate, the latter component being obtained by dehydration of disodium orthophosphate upon the calcining.

This catalyst is used to dehydrate 2-methyl-2,3-butanediol.

2-methyl-2,3-butanediol is passed over 10 cc of catalyst for a total period of time of 14 hours. The reaction is carried out at 500°C with an hourly space velocity of the diol, measured in liquid state, of 2.5. The diol is not diluted in the nitrogen in this test. It is used in pure form. The test was interrupted at the end of the seventh hour. The catalyst, without having been regenerated, served for another 7-hour test carried out under the same conditions.

EXAMPLE VI

This example concerns strontium pyrophosphate.

100 cc of hot solution of strontium nitrate containing 42.4 g of $Sr(NO_3)_2$ are poured into 100 cc of a boiling solution containing 44.6 g of sodium pyrophosphate decahydrate. The precipitate is filtered after it has been allowed to cool for half an hour. It is then dried for 18 hours at 110°C and then calcined at 400°C for 2 hours. A mixed sodium and strontium pyrophosphate is obtained.

This catalyst is used for the dehydration of 2-methyl-2,3-butanediol under the conditions described in Example I. The composition of the efflux is entered in Table VI.

TABLE VI

| Conversion of diol | 82.3% |
| --- | --- |
| Yield of isoprene | 6.0 |
| Yield of 2-methyl-1-butene-3-ol | 66.1 |
| Yield of 3-methyl-2-butylene-1-ol | 2.8 |
| Yield of trimethyl a acetaldehyde | 2.4 |
| Yield of methyl isopropyl ketone | 8.2 |

We claim:

1. In a method for dehydrating vicinal diols into diolefins and olefin alcohols, the improvement comprising contacting said vicinal diol under dehydration conditions, effected with said diol in the vapor phase, pure or diluted with an inert gas, at a temperature between 350° and 800°C, and with an hourly space velocity of between about 0.5 and 2.5, with a mechanically strengthened catalyst prepared by the method consisting essentially of forming an intimate mixture of finely divided solid particles of at least one pyrophosphate and at least one acid orthophosphate of at least one metal belonging to the group consisting of lithium, sodium, strontium, and barium into a formed mass in a proportion sufficient to give improved mechanical strength to the resulting catalyst and calcinating said mass at a temperature of between about 400° to 600°C to transform said acid orthophosphate into pyrophosphate.

2. A method according to claim 1, comprising recycling the olefin alcohols for dehydration to said diolefin.

3. A method according to claim 2, wherein said diol is 2-methyl-2,3-butanediol and said diolefin is isoprene.

4. A method according to claim 2, wherein said diol is 2,3-butanediol and said diolefin is butadiene.

5. A method according to claim 2 wherein the method for preparing said catalyst said phosphates are mixed in powdered form, wetted to form a paste, extruded, dried, and finally calcinated.

6. A method according to claim 3 wherein the method for preparing said catalyst said phosphates are mixed in powdered form, wetted to form a paste, extruded, dried, and finally calcinated.

7. A method according to claim 4 wherein the method for preparing said catalyst said phosphates are mixed in powdered form, wetted to form a paste, extruded, dried, and finally calcinated.

8. A method according to claim 3 wherein said dehydration temperature is between 400° and 500°C.

9. A method according to claim 4 wherein said dehydration temperature is between 400° and 500°C.

* * * * *